United States Patent [19]

Jestrich et al.

[11] Patent Number: 4,577,507

[45] Date of Patent: Mar. 25, 1986

[54] METHOD FOR THE ULTRASONIC TESTING OF DISCS SHRINK-FITTED ONTO SHAFTS IN VICINITY OF SHRINK-FITTED SEATS, AND APPARATUS FOR CARRYING OUT THE METHOD

[75] Inventors: Hans-Achim Jestrich, Ratingen; Ewald Werntgen, Mülheim, both of Fed. Rep. of Germany

[73] Assignee: Kraftwerk Union Aktiengesellschaft, Mülheim, Fed. Rep. of Germany

[21] Appl. No.: 613,902

[22] Filed: May 24, 1984

[30] Foreign Application Priority Data

May 24, 1983 [DE] Fed. Rep. of Germany ....... 3318748

[51] Int. Cl.$^4$ ........................................... G01N 29/04
[52] U.S. Cl. ....................................... 73/640; 73/619; 73/621
[58] Field of Search ................. 73/618, 619, 621, 640

[56] References Cited

U.S. PATENT DOCUMENTS

| | | | |
|---|---|---|---|
| 3,863,496 | 2/1975 | Hiramatsu | 73/640 |
| 4,117,733 | 10/1978 | Gugel | 73/640 |
| 4,140,954 | 2/1979 | Jeffras et al. | 73/619 |
| 4,474,064 | 10/1984 | Naruse et al. | 73/640 |

Primary Examiner—Howard A. Birmiel
Attorney, Agent, or Firm—Herbert L. Lerner; Laurence A. Greenberg

[57] ABSTRACT

A method for the ultrasonic testing of disc bodies, shrunk onto shafts, is especially adapted for testing the shrink-fitted seats thereof adjoining the shafts and usually is provided with anti-rotation holes containing anti-rotation inserts. Such disc body arrangements are often used in the field of low pressure turbine rotor disc fastenings. The method is carried out by using ultrasonic angle beam probes operating according to a method of corner reflection or transversal waves within the range of critical angles of total reflection, or according to a method of grazing incidence. Both methods can be used as a pulse echo technique, or as a tandem technique. The probes are coupled to the curved side walls of the discs for following test patterns extending in circumferential direction of the disc bodies. Ultrasonic sound beams emanating from the probes are aligned toward the test regions of the inner surfaces of the hubs. Three axially adjacent test regions are tested. The outer regions are tested with the angle beam probes according to the principle of the pulse echo technique, whereas the central test region is tested according to the principle of the tandem technique with at least two of the angle beam probes, by transmitting with one of the probes on one of the side walls and receiving with another one of the probes on the opposite side wall of the wheel discs. The invention also relates to an apparatus for carrying out the method.

23 Claims, 18 Drawing Figures

METHOD FOR THE ULTRASONIC TESTING OF DISCS SHRINK-FITTED ONTO SHAFTS IN VICINITY OF SHRINK-FITTED SEATS, AND APPARATUS FOR CARRYING OUT THE METHOD

BACKGROUND OF THE INVENTION

The invention relates to a method for the ultrasonic testing of discs shrink-fitted onto shafts in vicinity of shrink-fitted seats and adjoining material regions, especially in vicinity of inner surfaces of a hub and axial anti-rotation devices in wheel discs of low-pressure turbine rotors, the wheel discs having side walls being tapered in the radial direction from the inside out as seen in cross section, from the hub portion to a rim, substantially in the shape of a club.

The geometry of such wheel discs is extremely complicated for ultrasonic tests with ultrasonic probes (referred to below as a ultrasonic test and ultrasonic probes for short) of an inaccessible inner hub surface and the axial anti-rotation devices, especially axial anti-rotation holes. However, finding axially-radially oriented defects (such as stress corrosion cracks) at the inner surface of the hub and the axial anti-rotation devices is of great importance. The execution of reproducible ultrasonic tests encounters problems other than the one pointed out above concerning the complicated wheel disc geometry. This is due to the fact that only the side walls of the wheel discs are available as coupling surfaces for the ultrasonic probes. In most cases, the spacing between the rims of adjacent wheel discs is very small; thus, the spacing is at most 50 mm wide between the first and the second wheel disc of a low-pressure turbine rotor. The ultrasonic probes must be brought through this narrow gap and coupled to the side walls of the wheel disc. A further problem is that the sound paths leading to the axial anti-rotation devices and the sound paths leading to cracks which may be present and which start from them, are identical.

SUMMARY OF THE INVENTION

It is accordingly an object of the invention to provide a method for the ultrasonic testing of discs shrink-fitted onto shafts in vicinity of shrink-fitted seats, and apparatus for carrying out the method, which overcomes the hereinafore-mentioned disadvantages of the heretofore-known devices of this general type, which solves the stated problems and which meets the imposed test requirements. In other words:

possible stress corrosion cracks (axially-radially oriented defects) in vicinity of the inner surface of the hub and the axial anti-rotation devices in wheel discs shrink-fitted onto shafts can be determined as to location and size by means of an ultrasonic test in a reproducible manner;

100% of the inner surface of the hub and the axial anti-rotation devices and in particular, of the axial anti-rotation holes, can be tested for axially-radially oriented defects;

axially-radially oriented cracks with a radial depth of $\geq 5$ mm can be detected with certainty; and the ultrasonic test can be performed during the manufacture of the disc rotors, especially turbine rotors, as well as during an in-service inspection in the power generating station itself.

With the foregoing and other objects in view there is provided, in accordance with the invention, a method for the ultrasonic testing of the disc bodies, shrunk onto shafts; especially adapted for testing the shrink-fitted seats thereof adjoining the shafts and usually being provided with anti-rotation holes containing anti-rotation inserts. Such disc body arrangements are often used in the field of low pressure turbine rotor disc fastenings. The method is carried out by using ultrasonic angle beam probes operating according to a method of corner reflection of transversal waves within the range of critical angles of total reflection, or according to a method of grazing incidence. Both methods can be used as a pulse echo technique, or as a tandem technique. The probes are coupled to the curved side walls of the discs for following test patterns extending in circumferential direction of the disc bodies. Ultrasonic sound beams emanating from the probes are aligned toward the test regions of the inner surfaces of the hubs. Three axially adjacent test regions are tested. The outer regions are tested with the angle beam probes according to the principle of the pulse echo technique, whereas the central test region is tested according to the principle of the tandem technique with at least two of the angle beam prones, by transmitting with one of the probes on one of the side walls and receiving with another one of the probes on the opposite side wall of the wheel discs. There is also provided an apparatus for carrying out the method.

The advantages attainable through practicing the invention are in particular that a reliable ultrasonic test of the entire length of the shrinkage seat becomes possible, even in the case of a very complicated test geometry which exists in the case of wheel discs shrink-fitted onto shafts.

Tests according to the new method on a shrink-fitted test wheel disc which was provided with numerous test defects have demonstrated that axially-radially oriented defects at the inner surface of the hub and at the axial anti-rotation holes of low-pressure wheel discs, can be detected in the ultrasonic testing of the wheel discs in the shrink-fitted condition.

Other features which are considered as characteristic for the invention are set forth in the appended claims.

Although the invention is illustrated and described herein as embodied in a method for the ultrasonic testing of discs shrink-fitted onto shafts in vicinity of shrink-fitted seats, and apparatus for carrying out the method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

DESCRIPTION OF THE PREFERRED EMBODIMENTS

Figure 1:
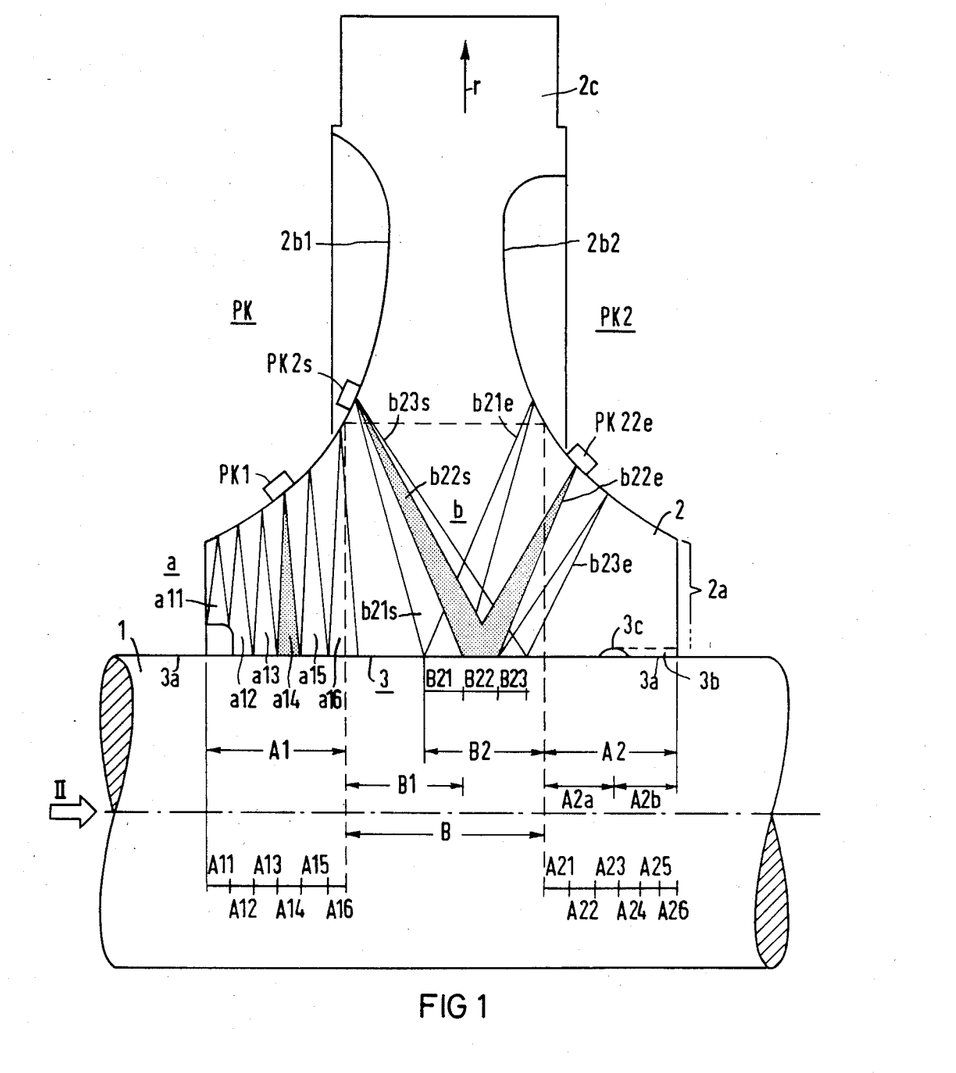
FIG. 1 is a fragmentary, diagrammatic, axialsectional view of the upper half of the wheel disc of a low-pressure turbine rotor, in which a portion of the hatching of the cross sectional area has been omitted for the sake of clarity, and wherein an ultrasonic angle beam probe and six ultrasonic sound beams are shown in an outer testing area A1 and, for insonification of a central test area B, two ultrasonic angle beam probes working according to the principle of the tandem technique are placed on two side walls of a wheel disc, and, for instance, three ultrasonic sound beams are shown.
Figure 15:
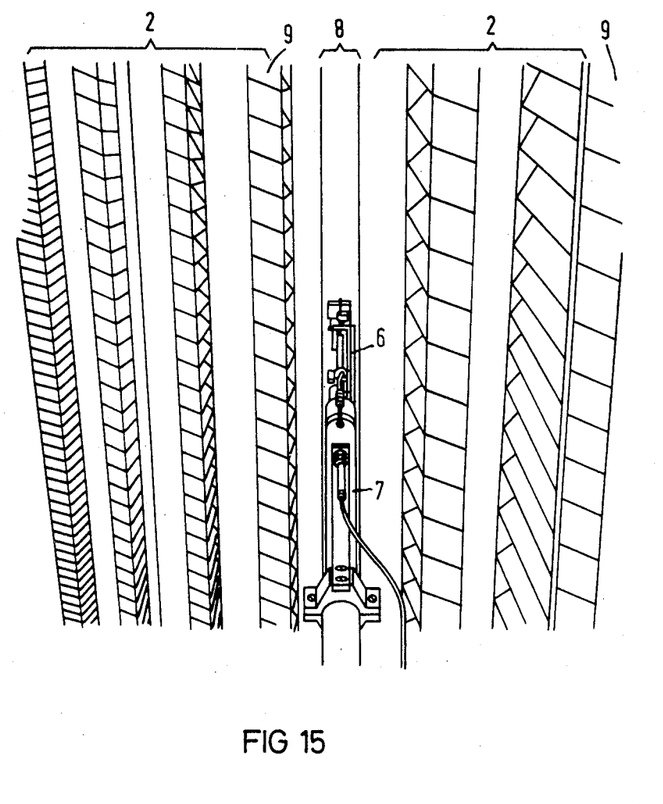
FIG. 15 is a perspective view of a portion of several axially aligned wheel discs shrink-fitted onto a shaft, wherein the manipulator arm with the probe mounting at its end is rotated into a position of minimum axial wheel-disc extent (loading position), in the axial gap between the wheel rims of two adjacent wheel discs.

Referring now to the figures of the drawing in detail, and first particularly to FIG. 1 thereof, there is seen a measuring apparatus for carrying out a method of ultrasonic testing of wheel discs or disc bodies 2 shrink-fitted on shafts 1 in vicinity of shrink-fitted seats 3 and adjoining material areas. The ultrasonic test relates in particular to the shrink-fitted seats 3 in vicinity of an inner surface 3a of a hub portion 2a and to axial anti-rotation devices 3b in the wheel discs 2 of low-pressure turbine rotors. In such cases, as represented by the cross-sectional view of FIG. 1, the wheel discs 2 have side walls 2b1, 2b2 which are tapered from the hub portion 2a thereof in the radial direction r from the inside to the outside approximately in the shape of a club down to a wheel rim 2c. This wheel disc geometry is extremely complicated when an ultrasonic test of the inaccessible inner surface 3a of the hub and of the axial anti-rotation devices 3b is to be carried out. Added to this difficulty is the fact that there is only a very small axial space provided between the wheel rims of the shrink-fitted discs, as seen in FIG. 15.

Figure 4:
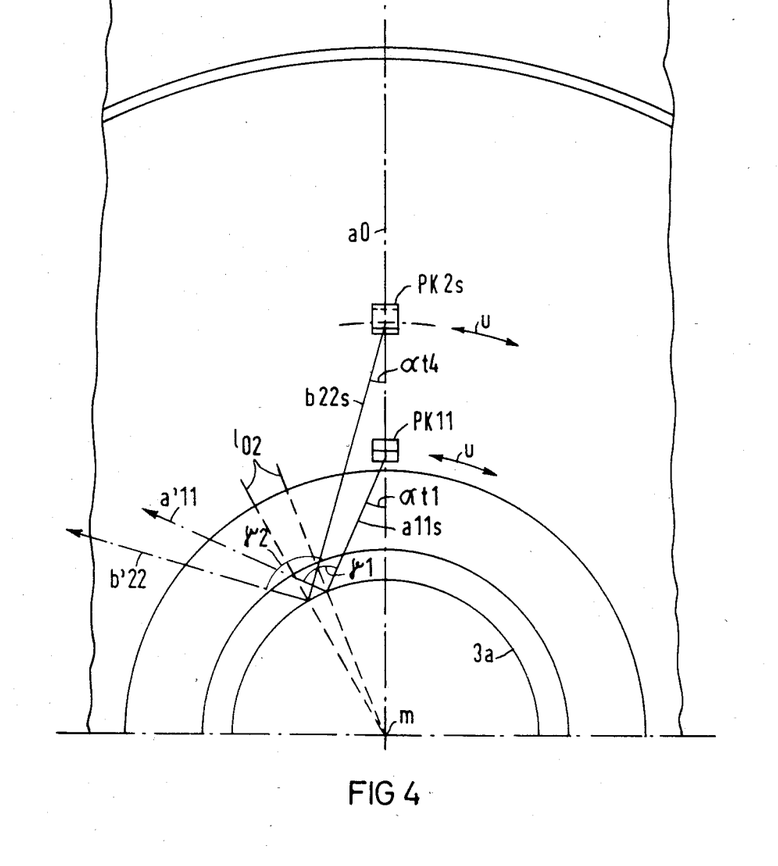
FIG. 4 is a fragmentary side-elevational view of the device as shown in FIG. 3, in which tangential incidence angles $\alpha_{t1}$, $\alpha_{t2}$ for obtaining the required angles of incidence $\gamma1$, $\gamma2$ can be seen, for the two probes shown in FIG. 3.

According to the method of the invention, ultrasonic probes are coupled at the side walls 2b1, 2b2. The ultrasonic probes are generally designated with reference symbol PK and are used for tracing tracks extending in the circumferential direction u, as seen in FIG. 4. The probes PK operate according to the principle of corner reflection of transversal waves in the incidence angle range of the total reflection, and an ultrasonic sound beam a or b thereof points to testing regions or areas A1 (first outer axial test region) and B (central axial test region) of the inner surface 3a of the hub. The beam can also be directed to a second axial test region A2. The phenomenon of total reflection of transversal waves in an incidence angle range of $35° \leq \gamma \leq 55°$ (corner effect) and the phenomenon of total reflection are known in the art.

Figure 2:
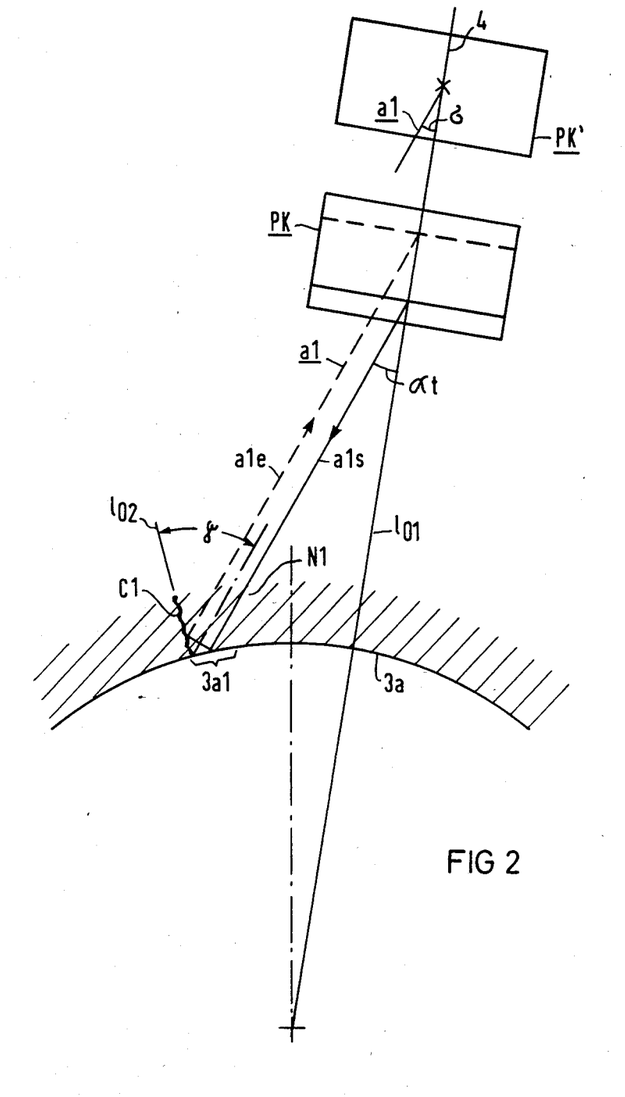
FIG. 2 is a fragmentary, cross-sectional view of a portion of a hub and probes showing the principle of corner reflection of transversal waves in the range of the angle of incidence of total reflection, as is utilized according to the invention if an axially-radially oriented defect is present in vicinity of the inner surface of the hub.
Figure 3:
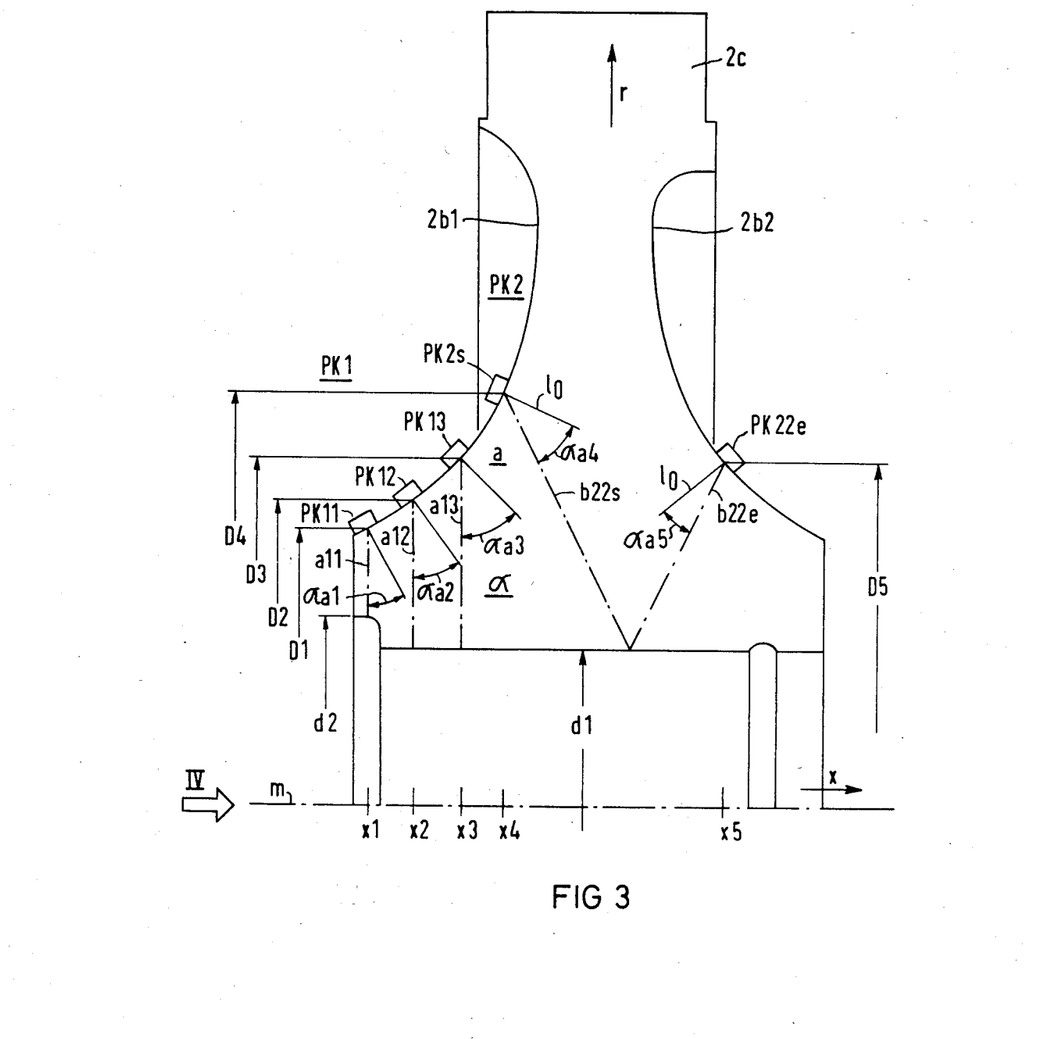
FIG. 3 is a view similar to a portion of FIG. 1, of a wheel disc with special importance being given to the presentation of the axial incidence angles with three ultrasonic angle beam probes which are placed on one side wall for "illuminating" an outer test area and which operate according to the principle of the pulse echo technique, and two ultrasonic angle beam probes which "illuminate" a central test area, which operate according to the principle of the tandem technique and which are each placed on a side wall.

These phenomena are utilized according to the invention for finding, localizing and interpreting substantially axially-radially oriented defects C1 shown in FIG. 2 which can be caused by stress corrosion. FIG. 2 diagrammatically illustrates how an ultrasonic beam a1s enters into the wheel disc 2 from an ultrasonic probe through a non-illustrated coupling surface and strikes a substantially 90° edge in vicinity of the inner surface of the hub 3a, which is formed by a section of the boundary 3a1 of the inner surface and an axially-radially oriented defect C1 is formed. As will be seen, the ultrasonic beams a1s will be reflected parallel to itself after a double reflection at the surfaces 3a1/C1 which form an edge or corner N1, and can be received again by the probe PK as a reflected beam a1e of a transversal wave according to the principle of pulse echo technique. In this case the probe PK is constructed as both ultrasonic transmitting and receiving probe. The ultrasonic beam is designated as a whole with reference numeral a1. FIG. 2 therefore represents a greatly diagrammatic view in the direction of the arrow II in FIG. 1 toward one end face of the wheel disc 2, while the tangential incidence angle $\alpha_t$ is also shown in FIG. 2. A line $1_o$ which is seen in FIG. 3 is a perpendicular to the sound entrance point of the ultrasonic beam a1s in vicinity of the coupling surface of the probe PK. If viewed in the direction of the axis, as in the views of FIG. 2 and FIG. 4, the tangential incidence angle $\alpha_t$ is obtained. If viewed in the direction normal to the axis, as in the views of FIG. 1 and FIG. 3, the axial incidence angle $\alpha_a$ is obtained. For the resulting incidence angle $\alpha$ which is subtended by the US beam a1s and the perpendicular $1_o$, the following relationship will apply:

$$\alpha = \tan^{-1}\sqrt{\tan^2\alpha_a + \tan^2\alpha_t}\ .$$

The incidence angle $\alpha$ must be distinguished from the oblique angle $\delta$ of the ultrasonic beam probes which is defined as the angle between the principle beam a1 projected on the test surface (2b1, 2b2) and the probe axis 4 which is parallel to the test surface, in the ultrasonic angle beam probes PK. The following relationship applies for the oblique angle $\delta$:

$$\delta = \tan^{-1}(\tan\alpha_a/\tan\alpha_t).$$

The oblique angle $\delta$ can be seen at the top of FIG. 2, in a top plan view onto the probe PK', while the probe PK is shown in a tilted position in accordance with the side wall contour. The angle of incidence $\gamma$ which in the examples given is preferably about 45°, is defined as the angle between the principal beam a1 and the normal $1_{o2}$ at the point of attack of the reflector. The angle of attack $\gamma \approx 45°$ is most favorable approximately in the range between 35° and 55°, as far as the echo amplitude is concerned. Similar conditions apply to the method of grazing incidence, in which case the angle of attack $\gamma$ is preferably about 90°.

Making reference again to FIG. 1, it is seen that the principal beams a are shown as concial ultrasonic sound beams, in order to indicate that each ultrasonic sound beam a or in detail, a11, a12, 13 etc. and b21, b22, etc. can sweep a certain axial subregion of the axial test areas A1, A2 and B. The inner surface 3a of the hub is subdivided, according to a further mode of the method invention, into at least three axial test regions: a central test region B and the two adjoining outer test regions A1, A2. Reference symbol A2b designates the area of the axial anti-rotation devices 3b which is separated from the shrinkage seat region 3 by a rounded lathe cut 3c. The axial anti-rotation devices may be in the form of slots having semicircular cross sections at the inner periphery of the hub. Disposed opposite these slots are corresponding semicircular slots at the outer periphery of the shaft 1. At this location round axial pins can be inserted or driven into the circular boundary surface channel formed in this manner and distributed at regular spacings over the outer periphery of the shaft 1 or the inner periphery of the hub 2, such as at five points. This zone or subregion of the axial anti-rotation devices must also be ultrasonically tested because surface stresses also exist in the vicinity of the axial anti-rotation devices.

The two outer axial test regions A1, A2 are then tested according to the principle of pulse echo technology with ultrasonic angle beam probes which are generally designated in FIG. 1 with reference symbol PK1 and designated in detail in FIG. 3 with reference symbols PK11 to PK13. In other words the ultrasonic beam or the ultrasonic sound beam of the respective probe PK1 which hits a defect C1 according to FIG. 2, encounters total reflection twice at the right-angle edge and is consequently reflected back parallel to itself, so that it returns to the probe PK1 and can be received there as a defect signal. As stated above, this applies to the test region A1 as well as to the test region A2, the latter including the subregion A2b (area of the axial anti-rotation devices 3b) and the subregion A2a (shrink-fit subregion).

The central axial test region B of the wheel disc 2, on the other hand, is tested according to the principle of the tandem technique with at least two ultrasonic angle beam probes PK, which are generally designated with reference symbol PK2 and are designated in detail with reference symbols PK21 and PK22. In the embodiment of FIG. 1, probe PK21 is the transmitter probe which is placed on the side wall 2b1, and probe PK22 is the receiving probe which is placed on the opposite side wall 2b2 of the wheel disc 2. The stippled ultrasonic sound beam formed of the ultrasonic sound beam b22s which is transmitted by the transmitter probe PK2s, is assumed to strike a defect in vicinity of the inner surface 3a of the hub and is therefore reflected to the receiver probe PK22e as the ultrasonic sound beam b22e. A reversal is also possible, i.e., wherein the probe PK22e is the transmitter probe and the probe PK2s is the receiving probe. The remaining US sound beams of the test region B, namely, b21s to b21e and b23s to b23e give expression to the fact that the entire central subregion B2 can be swept and covered. In comparison to the ultrasonic sound beams b22s to b22e for transmitting and receiving, the ultrasonic sound beams b21s to b22e and b23s to b23e, other probes PK2 with differing incidence angles $\alpha$ and oblique angles $\delta$ may be used, since their positioning on the side wall contour 2b2 is shifted on the receiver side and its position may also be shifted in some circumstances on the transmitter side at the side wall 2b1, as can be seen.

In order to find and ascertain defects which are situated in the axial subregion B1, it is sensible to couple the transmitting-receiving probe to the side wall 2b2 and to couple the receiver probes to the side wall 2b1, i.e., reversing the probe disposition shown on FIG. 1. Accordingly, the central test region B is subdivided into at least two overlapping subregions B1, B2. One subregion B2 (or B1, respectively) of these is insonified by transmitting probes PK2 which are disposed on the side wall 2b1 (or 2b2, respectively). The ultrasonic sound beam or the sound beam is therefore reflected in this case to the receiver probes PK22 which are disposed on the side wall 2b2 (or 2b1, respectively) adjoining the subregion B2 (or B1) and vice-versa.

As is illustrated by the ultrasonic sound beams a11 to a16, the outer test region A1 is also subdivided into several axial subregions which are designated with reference symbols A11, A12, etc., in accordance with the designation of the ultrasonic sound beams. Similarly, the other outer region A2 can also be subdivided even more finely than into the subregions A2a, A2b, namely, into the subregions A21, A22, etc. to A26. Each of these subregions A11, A12 etc.; A21, A22 etc. is tested by at least one ultrasonic angle beam probe. However, it has been found advantageous to use multiple probe mountings as far as possible, so that in this way more than one subregion can be tested.

In a similar manner to the fine subdivision of the outer test regions A1, A2, a fine subdivision for the central test region B2 in the form of subregions B21, B22 and B23 is shown in FIG. 1. The same type of subdivision applies to the central subregion B1, which may contain subregions B11, etc.

As seen in the axial direction, the individual subregions A11, etc., B11, B21 etc., A21 etc. have a width which is determined by the divergence of the sound fields and the magnitude or length of the sound paths between the coupling position of the probes PK at the wheel disc side wall 2b1 and 2b2 and the possible existing defect at the inner surface 3a of the hub. This width may be about 25 to 50 mm, for example.

In order to test such a subregion, it is always necessary to couple one (two for the tandem technique) ultrasonic angle beam probe which is determined by the geometric relationships of this subregion, at a very definite position of the wheel disc side wall 2b1, 2b2. By rotation of the wheel discs, the individual subregions then extend in the circumferential direction u over 360°.

As shown in FIG. 1 and even more clearly in FIGS. 3 and 4, a large number of probe positions are required at the wheel disc side walls 2b1, 2b2 to test 100% of the inner surface of the hub of the wheel discs 2. These positions are determined by axial coordinates which are individually designated with reference symbols x1, x2 etc. in the x-direction and by the radial coordinates in the r-direction. When discussing the radial coordinates, a distinction must be made between the test diameters $D_1$, $D_2$ on which the probes PK are disposed, and the diameters d1 (inside surface of the hub) and d2 (lathe cut at the end face), i.e., radial coordinates which are given by the shape of the wheel disc itself. The characteristic data of the probes PK, the incidence angle $\gamma$ and the oblique angle $\delta$ accordingly depend on the geometric relationships at the respective probe position. FIG. 3 illustrates several different axial incidence angles in the axial direction, referred to by reference symbol $\alpha_a$ in general, and designated by reference symbols $\alpha_{a1}$, $\alpha_{a2}$ etc. in particular, which depend on the individual probe positions. The incidence angle $\alpha$ and the oblique $\delta$ are a function of the radial coordinates D, d. This function may be abbreviated as: d, $\delta = f(D,d)$. This is the reason why the ultrasonic testing of, say, 10 wheel discs of a low-pressure rotor with about 160 test subregions, require about 40 special ultrasonic angle beam probes and about 50 different probe mountings, even after optimization. In FIG. 3, the probe operating according to the principle of the pulse echo technique (wherein one probe serves for transmitting an ultrasonic beam and at the same time for receiving the reflected ultrasonic beam) are designated in general with reference symbol PK1 and are designated individually with reference symbols PK11, PK12 and PK13, depending on their position on the side wall. The probes operating according to to principle of the tandem technique are generally designated with reference symbol PK2 and are individually designated with reference symbols PK2s (transmitting probe) and PK22e (receiver probe). The reference symbols given to the individually designated ultrasonic beams and ultrasonic sound beams, a11, a12, etc., b21, b22 etc. coincide with the reference symbols of the corresponding axial test subregions and probes PK1, from which these ultrasonic beams originate or, in the case of the probe PK22e, at which they are received. Since the probe which serves for carrying out the tandem test is shown in common for three US beams b21, b22, b23 and their subregions B21, B22, B23, it has been designated with reference symbol PK2s. The axial incidence angles $\alpha_{a1}$ to $\alpha_{a4}$, shown in FIG. 3, are in the range between 30° and 50°, and the axial incidence angle $\alpha_{a5}$ of the receiver probe PK22e is about 20°.

The incidence angles $\alpha_{t1}$ of the probe PK11 and $\alpha_{t4}$ of the probe PK2s shown in FIG. 4 are about 20° and 15°, respectively, and become smaller as the distance from the probe to the center m of the shaft increases. The corresponding angle of incidence $\gamma$ in FIG. 2 is about 45° and the corresponding angles of incidence $\gamma1$ and $\gamma2$ are about 90° according to the presentation of FIG. 4. The US beam a11s starting from the probe PK11 in FIG. 4 is subjected to total reflection at the inner boundary surface of the hub and does not return to the probe PK11 if no defect is present, but instead continues its path as an irrelevant reflection beam a'11 in the wheel disc until its total attenuation. The same applies to the US beam b22s originating from the probe PK2s. If a defect is present, this beam would be received by the probe PK22e as a beam which was totally reflected twice as shown in FIG. 3. In FIG. 4, on the other hand, it is assumed that no defect is present at the inner periphery of the hub and while this beam b22s is reflected totally once, this reflection does not occur a second time, so that it propagates in the wheel disc 2 as an irrelevant reflected beam b'22 until it is extinguished.

Figure 5:
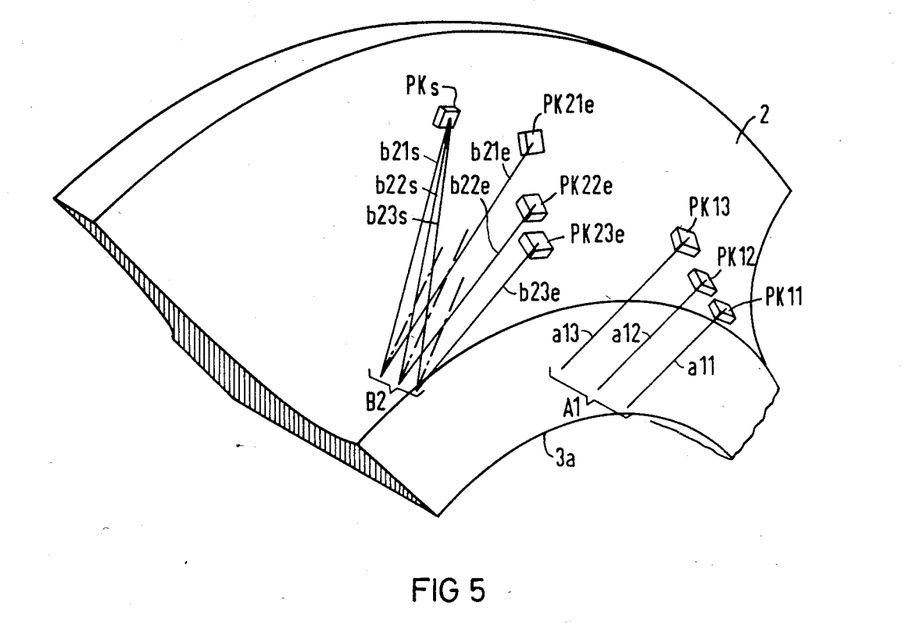
FIG. 5 is a fragmentary perspective view of a transparent model of a wheel disc segment, showing the reflection relations in the case of corresponding defects for the basic testing apparatus according to FIGS. 3 and 4, wherein additionally three different receiver probes are shown instead of one, each of which belong to a particular incidence angle and oblique angle of the transmitter probes, with the probes operating in accordance with the tandem principle.

For a better understanding, the relationships are presented once more in FIG. 5 with the aid of a transparent plastic model, and it is assumed that corresponding defects exist at the inner periphery of the hub 3a, which cause double total reflection in vicinity of the edge, as explained with the aid of FIG. 2. The ultrasonic angle beam probe operated according to the pulse echo technique are again designated with reference symbols PK11, PK12 and PK13 as in FIG. 3, as are the corresponding ultrasonic beams a11, a12, a13. Each of these ultrasonic beams can be thought of as being composed of a transmitting beam a1s formed of beams a11s, a12s, a13s and of a beam a1e formed of beams a11e, a12e, a13e which is reflected in the defect edge vicinity and returned to the probe, as seen in FIG. 2. The double beams are not shown for the probes PK11 to PK13 for the sake of simplicity; however, they are shown for the probe PKs (transmitting probe) and PK21e to PK23e (receiver) operating in accordance with the tandem technique. Starting from the probe PKs, three different US beams B21s, b22s and b23s which have incidence angles $\alpha$ and oblique angles $\delta$ that differ from each other, in such a manner that the test subregion B2 can be swept by their ultrasonic sound beams, can be seen. In order to receive the ultrasonic beams or ultrasonic sound beams which are reflected twice, the positioning of the receiver probes PK21e to PK23e also changes as shown at the corresponding defect corners; the associated ultrasonic beams or sound beams received by the receiver probes are designated with reference symbols b21e, b22e and b23e. The axial testing subregion swept by the test heads PK11 to PK13 is again designated with reference symbol A1.

Figures 6, 7:
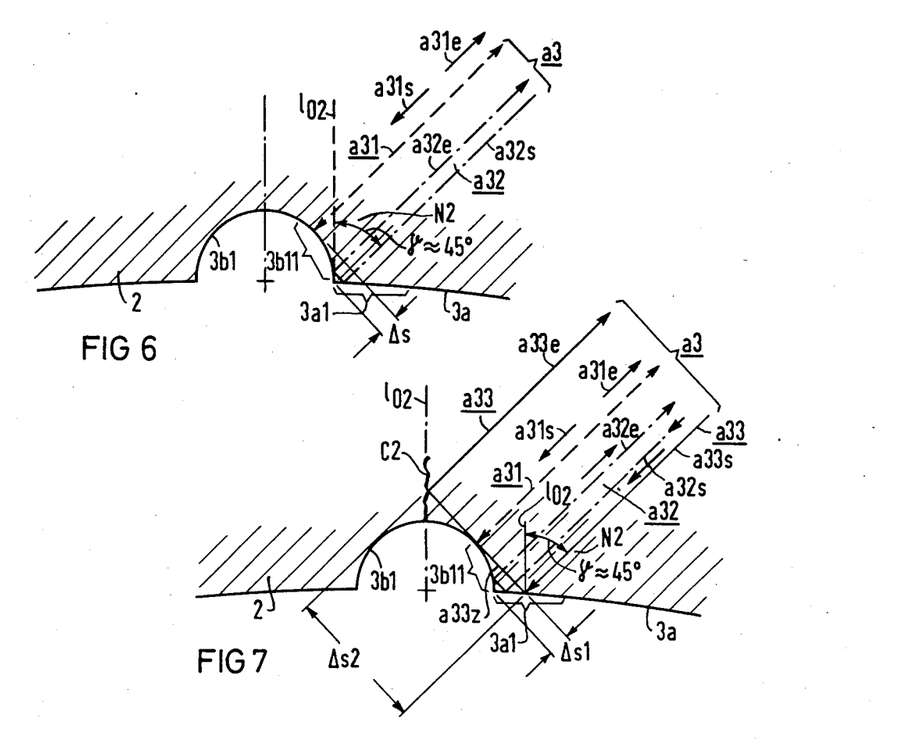
FIG. 6 is a fragmentary, cross-sectional view of a hub with an anti-rotation hole without a defect, wherein the physical principle shown in FIG. 2 is utilized for the detection of defects in vicinity of axial anti-rotation holes in the periphery of the inner hub of a wheel disc.
FIG. 7 is a view similar to FIG. 6 with the difference that a defective anti-rotation hole is present and therefore, a third echo (the defect echo) is obtained in comparison with FIG. 6.

FIGS. 6 and 7 show the US reflection relationships in vicinity of an axial anti-rotation hole 3b1 in a view corresponding to FIG. 2. More specifically, in FIG. 6 these relationships are shown for a hole without a defect and in FIG. 7 they are shown under the assumption that an axially-radially oriented fault C2 is present which extends from the inner periphery of the semicircular hole 3b1 into the hub or disc body 2 over about 5 to 10 mm. This hole 3b 1 which has a semicircular cross section, should be thought of as being disposed in vicinity of the axial anti-rotation device 3b according to FIG. 1. FIG. 6 will be described first. It will be assumed with regard to FIG. 6 that an ultrasonic sound beam starts at an incidence angle $\alpha$ and at an oblique angle $\delta$ originating from a suitable non-illustrated ultrasonic probe, so that it arrives in vicinity of the edge or corner N2 at an angle of incidence $\gamma \approx 45°$. The corner N2 is bounded by the partial portion 3a1 of the boundary of the inner periphery or surface 3a of the hub and an arc section 3b11 of the semi-cylindrical boundary surfaces of the axial anti-rotation hole 3b1. The ultrasonic sound beam a3 can be thought of as being divided into first and second sub-bundles a31 and a32. The first beam sub-bundle a31 which is reflected into itself at the periphery of the hole at an angle of incidence of approximately 90°, and the second sub-bundle a32 which is totally or corner-reflected in vicinity of the corner. In order to illustrate the physical relationship, the sound sub-beam a32 is further subdivided into two individual sub-beams a32s (transmitting beam) and a32e (receiver beam, which is totally reflected twice in the corner). With respect to the sub-beam a31, the sub-beam a31s travels toward the circumference of the hole and the sub-beam a31e which is reflected at the boundary surface returns from there, in directions which are indicated by arrows. Reference symbol $\Delta s$ represents the one-time path difference between the radiation sub-beams a31 and a32. The partial beam a32 must travel a distance during the forward and return run which is about 2 times $\Delta s$ longer than the distance traveled by the beam a31, which is the motion or sound path difference.

As far as possible, the same reference symbols are used in FIG. 7 as in FIG. 6. Through a comparison it has been determined that due to the axially-radially oriented fault C2, an ultrasonic beam a33s which normally would become lost after one total reflection in the edge region (with an angle of incidence $\gamma \approx 45°$) is instead totally reflected at the fault boundary surfaces a second time according to the corner reflection effect and can therefore be received as a reflected beam a33e by the probe representing a defect signal. A partial section, extending tangentially to the hole 3b1 of the US beam designated as a whole with reference symbol a33, is given reference symbol a33z.

Figure 9A:
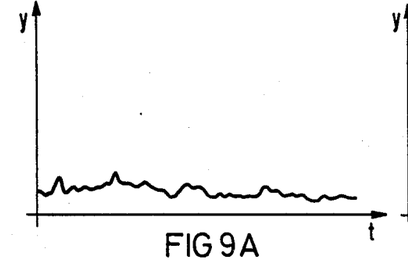
FIG. 9A is a diagram representing a photo of the screen of a CRT of an oscilloscope, taken during the ultrasonic test of an inner surface of a hub without a defect.
Figure 9B:
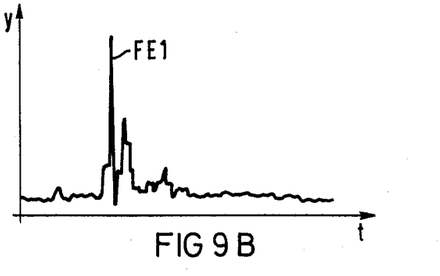
FIG. 9B is a diagram representing photo of the screen of a CRT of an oscilloscope with a an ultrasonic indication which comes from an axially-radially oriented defect at the inner surface of the hub (as seen in FIG. 2)
Figure 10A:
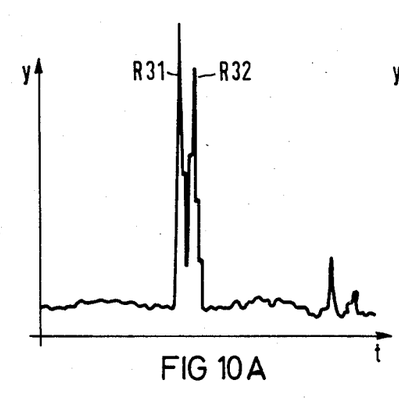
FIG. 10A is a diagram representing a photo of the screen of a CRT of an oscilloscope with two ultrasonic indications from an axial anti-rotation hole according to FIG. 6 without a defect.
Figure 10B:
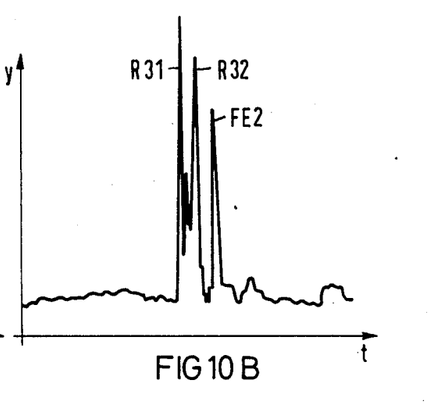
FIG. 10B is a diagram with three ultrasonic indications from a defective axial anti-rotation hole according to FIG. 7.

FIGS. 9 and 10 show examples of ultrasonic displays on a screen which are seen as simplified curves of a graph, the amplitude y being plotted on the ordinate axis and the time t on the abscissa axis. FIG. 9A represents a photo of the screen of a CRT of an oscilloscope for the ultrasonic test of an inner surface of the hub without a defect (no defect signal is received as seen, for instance, in FIG. 4). FIG. 9B represents a photo of the screen of a CRT of an oscilloscope with a ultrasonic display of an axially-radially oriented fault of the inner hub surface 3a, which could represent the fault location C1 of FIG. 2. A defect echo FE1 is shown by the largest spike.

In FIG. 10A, a photo of the screen of a CRT of an oscilloscope with two ultrasonic displays R31 and R32 of an axial anti-rotation hole without a defect according to FIG. 6 is shown, the display R31 belonging to the ultrasonic beam a31 and the display R32 belonging to the ultrasonic beam a32. In accordance with the sound path difference of approximately twice $\Delta s$, the display R32 is somewhat delayed relative to the display R31.

In FIG. 10B, a photo of the screen of a CRT of an oscilloscope with three ultrasonic displays R31, R32 and FE2 from a defective axial anti-rotation hole according to FIG. 7 is shown. Thus, the defect display FE2 which belongs to the reflective ultrasonic beam a33e has been added in comparison to FIG. 10A. The beam a33e has a sound path difference of $\Delta s_2$ seen in FIG. 7 in comparison with the beam a31 arriving at 90°, while the ultrasonic display R32 corresponding to the ultrasonic beam a32, has a sound path difference of approximately twice $\Delta s_1$ from the ultrasonic a31. The sound path differences $\Delta s_1$ and $\Delta s_2$ are indicated diagrammatically in FIG. 7.

Figure 8:
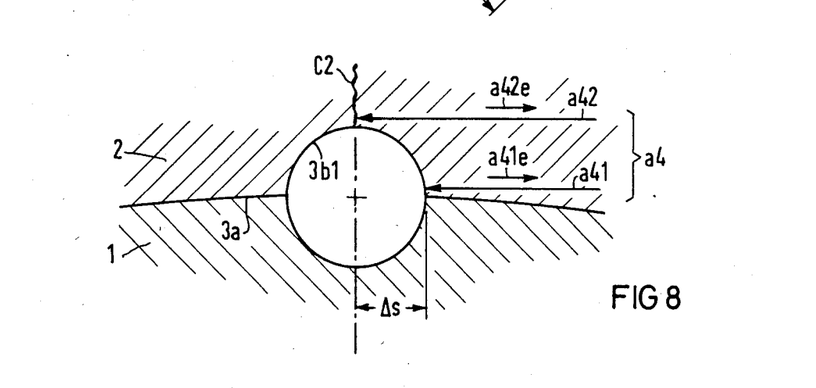
FIG. 8 is a fragmentary cross-sectional view of a hub illustrating another testing principle for detecting defects in vicinity of the axial anti-rotation devices with "grazing incidence" of the ultrasonic sound beams (in contrast thereto the test principle shown in FIGS. 2, 6 and 7 is referred to as the corner reflection method)
Figure 11A:
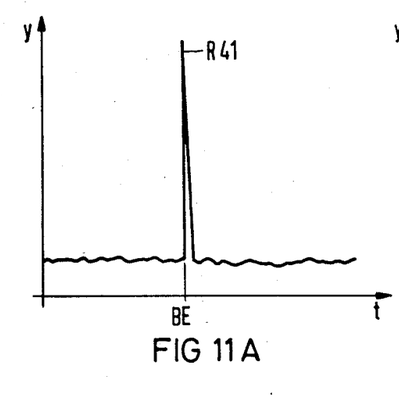
FIG. 11A is a diagram of a drill hole echo with an anti-rotation hole without a defect, obtained from a photo of the screen of a CRT of an oscilloscope using the method of grazing incidence according to FIG. 8.
Figure 11B:
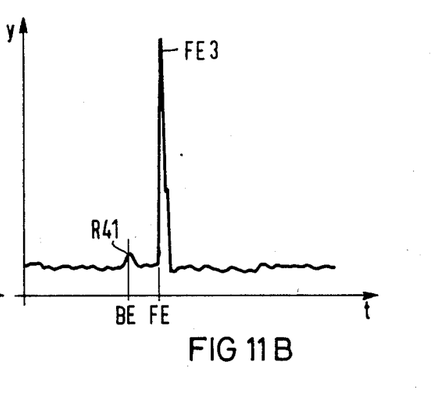
FIG. 11B is a diagram of a defect echo resulting from a defect in the anti-rotation hole according to FIG. 8 which is substantially larger than the hole echo, so that the signal amplification has had to be reduced.

In addition to, or instead of, the corner reflection method according to FIGS. 6, 7 and 10, a grazing incidence of the ultrasonic radiation beams can also be used for determining axially-radially oriented defects in vicinity of the axial anti-rotation devices, especially the anti-rotation holes according to FIG. 8. In FIG. 3, the US radiation beam is generally designated with reference symbol a4; the beam falls in a "grazing" manner with respect to the inner surface 3a of the hub from the outside onto a quadrant of the entire anti-rotation hole 3b1 which extends over 360°. The upper semi-cylinder of the hole 3b1 is located in the wheel disc 2, and the lower semi-cylnder thereof is in the shaft 1. In the absence of faults, only one hole echo R41 is obtained according to FIG. 11A, the time marker of which is designated with reference symbol BE. The echo R41 belongs to the returning ultrasonic sub-beam a41e seen in FIG. 8. The angle of incidence of this subbeam a41 onto the periphery of the hole is approximately 90°. As may further be seen from FIG. 8, the sub-beam a42 is also reflected at the resilient boundary surface in the event of the fault C2, at an angle of incidence of 90°, so that a ultrasonic fault display in the form of the fault echo FE3 according to FIG. 11B is obtained. Since the amplitude of this defect echo is relatively large, the amplification of the display equipment must be reduced as compared to that used in FIG. 11A, so that the hole echo R41 has been reduced to a small bump. In most cases for determining axially-radially oriented defects in vicinity of the anti-rotation devices, this clear differentiation between the fault echo and the hole echo in the method of grazing incidence makes the echo appear in a more suitable manner than in the corner reflection method according to FIGS. 6, 7 and 10. It is an advantage, however, that both methods can be used for difficult defect interpretations. Naturally, the incidence angle $\alpha$ and the oblique angle $\delta$ of the ultrasonic probes must be chosen differently in the case of the grazing incidence according to FIG. 8 than in the corner reflection method according to FIGS. 6 and 7.

Making reference to FIG. 1, the selection criteria for the transition from an outer test region A1 or A2, respectively, to a central test region B or B1, B2, respectively, and therefore for the transition from the pulse echo technique to the tandem technique, will be discussed briefly.

As one criterion, a calculation angle α at the respective coupling point, which should be at most equal to or smaller than 75°, and preferably less than 70°. The reason for this criterion is that, if the limits are exceeded, the construction of suitable probes with corresponding incidence angles α encounters difficulties.

As already explained in connection with FIG. 3, special angle probes with matched incidence angles α and oblique angles δ are used as a function of the respective transmitting and/or receiving position of the probes PK on the sidewall contour 2b1 or 2b2, given by axial and radial coordinates x, r. As is shown in detail in FIG. 12, these special angle probes PK together with measuring feelers 5 are disposed on a probe mounting 6 which is matched to the respective sidewall section and has a template 6a. As shown in detail in FIG. 13, the probes PK are disposed at a free extensible end 7a of a manipulator arm 7 and are brought to the contour of the respective sidewall 2b2 (2b1) to be coupled. Each of the templates is assigned to a given axial sub-region $A_i$, $B_i$ of the test region A1, B, B1, B2, A2 (if 10 wheel discs are tested, about 15 different templates are required) and its axially and radially correct position is indicated by the measuring feelers 5. In other words, the measuring feelers which are constructed in particular as inductive measuring feelers, are disposed on each template 6a for monitoring the positioning of the angle beam probe and the probes themselves. This is always done in very well defined positions and relationships relative to each other, so that when coupling at the defined position of a wheel disc sidewall, the conversion of the incidence and squint angles of the respective probes into the incidence directions required for the definite test regions is ensured.

Figure 12:
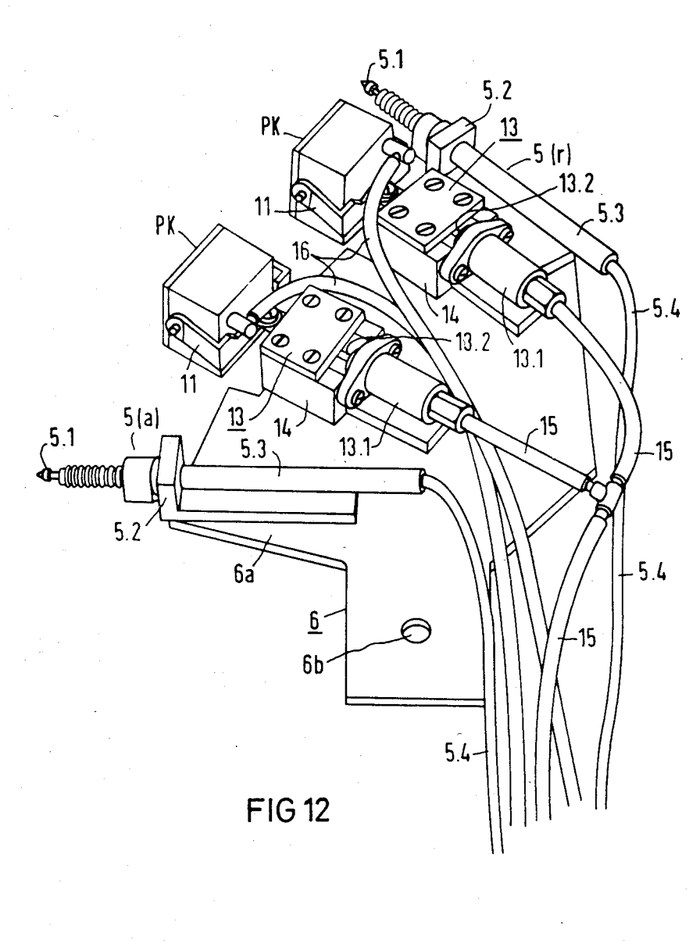
FIG. 12 is a perspective view of a probe mounting if a template with two ultrasonic angle beam probes fastened thereto as well as two corresponding measuring feelers including associated pneumatic, hydraulic and electrical supply lines.
Figure 13:
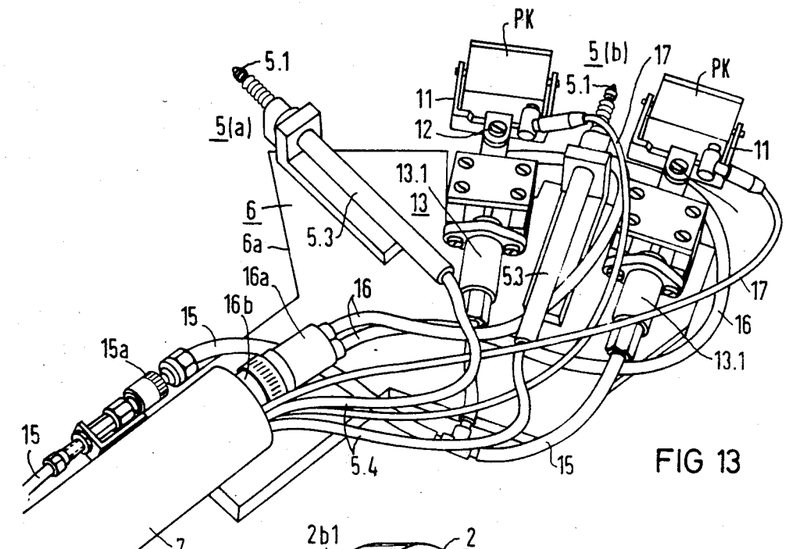
FIG. 13 is a view similar to FIG. 12 of probes mounted at the end of a manipulator arm and placed on the side wall of a wheel disc.

For simplifying the test method, i.e. in particular for the reduction of the required test manipulations, it is advantageous if the outer axial test regions A1, A2 are tested at least partially with special angle beam probes PK which are fastened at least in pairs to the corresponding probe mountings 6 and can be positioned together with the mountings at the corresponding sidewall portion of the wheel disc 2, as is shown in FIGS. 12 and 13.

Figure 14:
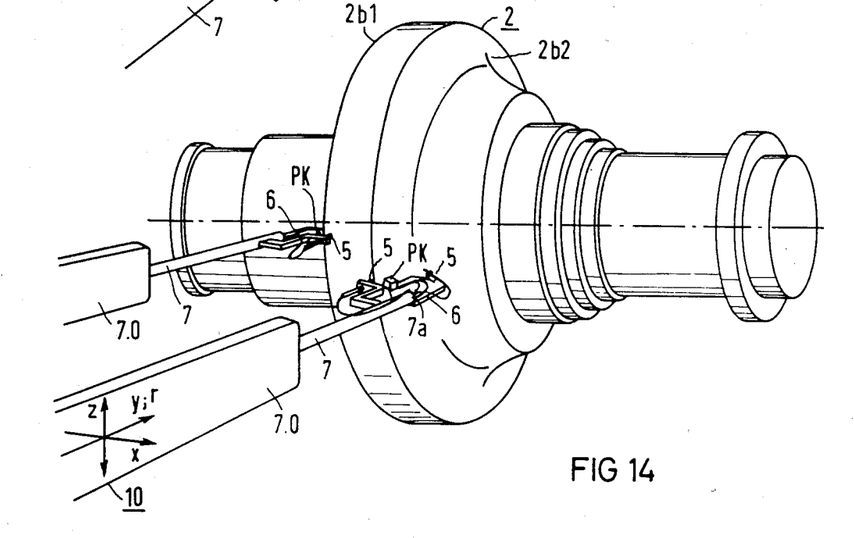
FIG. 14 is a perspective view showing two manipulator arms each being provided at the ends thereof with a probe mounting as shown in FIGS. 12 and 13, and each being positioned and coupled to one side wall of a test wheel disc for carrying out the test method according to the principle of the tandem technique.

FIGS. 13 and 14 illustrate that the probe mountings 6 with their probes PK are moved in the radial and in particular, in the radial-horizontal direction of the respective wheel disc 2, to the contour of their sidewalls 2b2, 2b1.

As already indicated in connection with FIG. 15, the probe mounting 6 is first rotated at its manipulator arm 7 into a position of minimum axial extent of the wheel disc, if narrow axial gaps 8 are present between adjacent wheel discs 2, and the mounting 6 is brought through the narrow gap 8 into this position of rotation, as seen in FIG. 15. Only then, is the probe mounting 6 turned into a superimposed position, as can be seen, for instance, from FIG. 13. In FIG. 15, the blade rims of the two wheel discs 2, 2 adjacent each other with a narrow axial gap, are designated with reference numeral 9. These blade rims 9 are filled or inserted into corresponding circumferential slots formed in the wheel disc rim 2c, seen in FIGS. 1 and 3. For the sake of simplification, these circumferential slots are not shown in FIGS. 1 and 3. However, the axially projecting wheel rim is seen which would project axially even farther in the example according to FIG. 15 than would correspond to the presentation in FIGS. 1 and 3.

The apparatus for carrying out the method as a whole is seen best from FIG. 14. A manipulator 10 with at least one manipulator arm 7 is supported within a support arm 7.0 so that it can be moved in and out in the direction y or r, respectively. The arm 7 is therefore a telescopic arm which can be additionally rotated about its own longitudinal axis, as already explained. The coordinate y applies in general for the in-and-out movement; the coordinator r applies in case the manipulator arm 7 is moved in or out on a diameter of the wheel disc 2. Two manipulator arms 7 shown in FIG. 4 together with their support arms 7.0, are always adjustable not only in the direction y and r as is illustrated by the coordinate axes shown, but also in the x direction (longitudinal coordinate) and in the z direction (height coordinate), in both the plus and minus directions. In the exact respective coupling position, if the probe mountings 6 with their probe PK or a plurality thereof are coupled to the sidewall 2, this adjustment position is fixed at the manipulator 10, and the respective wheel disc 2 can be rotated slowly for sweeping the test tracks extending in the circumferential direction u. If the wheel discs are suitably accessible toward the outer periphery of the wheel discs, a manipulator 10 can be provided. The arm of the manipulator can be moved in and out and can also be adjusted in the circumferential direction u about the axis m of the wheel disc 2 in FIG. 3, or at least about a part of the circumference.

Referring to FIGS. 12 and 13, it has already been explained that different probe mountings 6 with their templates 16 can be interchangeably fastened to the free end of the manipulator arm 7. In this case, the templates 6a with the special angle beam probes PK and the measuring feelers are fitted to the sidewall contour of the respective axial subregion $A_i$, $B_i$ of the test regions A1, B, B1, B2, A2. According to FIGS. 12 and 13, at least two measuring feelers 5 are fastened to the probe mounting 6, one for the radial and the other for the axial position control. In FIGS. 12, 13, the right-hand measuring feeler always serves for the radial position control and the left-hand measuring feeler always serves for the axial position control, which is clarified by the characters r and a in parentheses. Thus, both measuring feelers are calibrated so that they deliver the corresponding position acknowledgement signal if the probe PK has occupied their exact coupling position. In principle, a still further non-illustrated measuring feeler could be provided, to serve for obtaining a control signal, or a likewise non-illustrated further control measuring feeler could be assigned to each of the two measuring feelers 5 in FIG. 12. These measuring feelers 5 are preferably inductive measuring feelers with axially spring-loaded feeler pins 5.1. The ends of the feeler pins facing away from a probe 5.2 support a magnet core which serves for the distance-dependent detuning of a non-visible induction coil apparatus that is disposed within tubular sleeves 5.3. Electric connecting cables of the distance transmitters 5 are designated with reference symbol 5.4.

The special angle beam probes are supported in gimbal bearings. In FIG. 12, a fork 11 which serves this purpose is seen, and in FIG. 13, a joint 12 crossing a shaft of the fork joint of the probe is seen to be supported at the piston rods of a pneumatic spring device 13. A pneumatic cylinder 13.1 of the pneumatic spring device 13 with a piston 13.2, is fastened or flanged on to small brackets 14 is such a manner that the probes PK can be pushed against their coupling surfaces if the penumatic cylinders 13.1 are activated. The small brackets 14 are bolted to the templates 6*a*; the corresponding pneumatic lines which lead to the cylinders 13.1, are designated with reference numeral 15. FIGS. 12 and 13 also show hose lines 16 for a coupling liquid, which are connected to a feed hose 16*b* through a pressureproof coupling section 16*a*. The feed hose 16*b* extends through the hollow manipulator arms 7 together with cables 5.4; the pneumatic lines 15 are similarly installed in the manipulator arm 7, with the insertion of a pneumatic coupling 15*a*. In order to permit fastening at the free end of the manipulator arm, the template 6*a* of the probes mounting 6 has a hole 6*b* formed therein. Electric signal lines 17 of the US probes PK are shown in FIG. 13, but not in FIG. 12.

The foregoing is a description corresponding, in substance, to German Application P No. 33 18 748.7, dated May 24, 1983, International priority of which is being claimed for the instant application, and which is hereby made part of this application. Any material discrepancies between the foregoing specification and the specification of the aforementioned corresponding German application are to be resolved in favor of the latter.

There are claimed:

1. Method for the ultrasonic testing of the disc bodies, shrunk onto shafts; the disc bodies having shrink-fitted seats adjoining the shafts, a shrinkage influence zone adjoining the seats, hubs having inner surfaces adjoining the shafts, two-sided wheel discs adjoining the hubs, axial anti-rotation devices in the wheel discs, a rim of the wheel discs, and side walls of the wheel discs tapered radially outwardly from the hub to the wheel disc rim as seen in cross section, the axial anti-rotation devices having boundary surfaces with anti-rotation holes formed therein; which comprises:

(a) ultrasonic angle beam probes operating according to a method of transversal wave reflection within a corner within the range of critical angles of total reflection, hereinafter referred to as corner reflection method, a grazing incidence method based on a grazing incident beam reflection principle, where both methods can be used as a pulse echo technique or as a tandem technique;

(b) coupling the angle beam probes to the side walls for following tast patterns extending in circumferential direction of the disc bodies, aligning ultrasonic sound beams emanating from the angle beam probes towards the test regions of the inner surfaces of the hubs;

(c) determining the presence of axially-radially oriented defects in the disc bodies with at least one of the corner reflection and grazing incidence method wherein in applying the corner reflection method a portion of an ultrasonic beam insonifying the boundary surface of the axial anti-rotation devices returns to a receiving angle beam probe only in the case of the total beam reflection within the corner formed by a boundary surface and a defect area and does not return in the absence of defects and wherein in applying the grazing incidence method the ultrasonic beam insonifying the boundary surfaces of the axial anti-rotation devices in a grazing manner creates a first hole echo in the absence of defects due to a 90° angle of incidence and creates a second echo in addition to the first echo having a substantially larger amplitude than the first echo in the presence of a defect due to an angle of incidence of substantially 90° at surfaces bordering the defect;

(d) subdividing the inner surface of the hub into at least three axial test regions including a central test region and two adjoining outer test regions;

(e) testing the outer test regions with the angle beam probes according to the pulse echo technique; and (f) testing the central test region according to the tandem technique with at least two of the angle beam probes, by transmitting with one of the angle beam probes on one of the side walls and receiving with another of the angle beam probes on the other side wall of the wheel discs.

2. Method for the ultrasonic testing of disc bodies, shrunk onto shafts; the disc bodies having shrink-fitted seats adjoining the shafts, a shrinkage influence zone adjoining the seats, hubs having inner surfaces adjoining the shafts, two-sided wheel discs adjoining the hubs, a rim of the wheel discs, and side walls of the wheel discs tapered radially out wardly from the hub to the wheel disc rim as seen in cross section which comprises:

(a) ultrasonic angle beam probes operating according to a method of transversal wave reflection within a corner within the range of critical angles of total reflection, hereinafter referred to as corner reflection method, a grazing incidence method based on a grazing incident beam reflection principle, where both methods can be used as a pulse echo technique or as a tandem technique;

(b) coupling the probes to the side walls for following test patterns extending in circumferential direction of the disc bodies, aligning ultrasonic sound beams emanating from the probes towards the test regions of the inner surfaces of the hubs;

(c) subdividing the inner surface of the hub into at least three axial test regions including a central test region and two adjoining outer test regions;

(d) testing the outer test regions with the angle beam probes according to the pulse echo technique; and (e) testing the central test region according to the tandem technique with at least two of the angle beam probes, by transmitting with one of the probes on one of the side walls and receiving with another of the probes on the other side wall of the wheel discs.

3. Method according to claim 2, wherein the boundary surfaces of the axial anti-rotation devices have anti-rotation holes formed therein, which comprises insonifying the anti-rotation holes and the boundary surfaces.

4. Method according to claim 1, which comprises subdividing the central test region into at least two overlapping subregions, insonifying one of the subregions with the transmitting angle beam probes, and reflecting the sound beam in the event of a defect to the receiving angle beam probes adjoining another of the subregions.

5. Method according to claim 1, which comprises subdividing the outer test regions into a plurality of axial subregions and testing each of the axial subregions with at least one of the angle beam probes.

6. Method according to claim 5, including a manipulator arm with a free extensible end, a probe mounting attached to the free end of the manipulator arm and fitted to a given section of the side wall, a probe mounting comprising a template, measuring feelers disposed on the probe mounting, and special angle beam probes disposed on the probe mounting with the feelers, which comprises assigning each of the templates to a respective subregion of the test regions, indicating a correct axial and radial position of the template with the measuring feelers, bringing the special angle beam probes and the measuring feelers to the contour of the given section of the side wall with the manipulator arm, coupling the special angle beam probes to the contour of the side wall, and adapting incidence angles and oblique angles of the special angle beam probes to the position of the special angle beam probes on the contour of the side wall to which the special angle beam probes are coupled with respect to axial and radial coordinates.

7. Method according to claim 6, which comprises fastening at least two of the special angle beam probes to a respective mounting, positioning the special angle beam probes at corresponding side wall portions of the wheel disc, and testing at least one part of the outer regions with the special angle beam probes.

8. Method according to claim 1, which comprises setting the incidence angle at the respective position at a maximum of 75°, as a criterion for the transition from an outer to a central test region and therefore from the pulse echo technique to the tandem technique and vice versa.

9. Method according to claim 1, which comprises setting the incidence angle at the respective position at less than 70°, as a criterion for the transition from an outer to a central test region and therefore from the pulse echo technique to the tandem technique and vice versa.

10. Method according to claim 6, which comprises carrying out the step of bringing the special angle beam probes to the side wall in the radial direction.

11. Method according to claim 6, which comprises carrying out the step of bringing the special angle beam probes to the side wall in the radial horizontal direction.

12. Method according to claim 6, wherein the wheel rims of adjacent wheel discs have narrow axial gaps formed therebetween, which comprises initially rotating the angle beam probe mounting at the manipulator arm into a position of minimum extend of the wheel disc in axial direction, subsequently bringing the mounting through the gap, and finally rotating the mounting into a position superimposed on the wheel rims.

13. Method according to claim 3, including axial anti-rotation pins inserted in the anti-rotation holes formed in the boundary surfaces between the hub and the shaft, which comprises insonifying a corner adjoining the inner periphery of the hub with the corner reflection method at an angle of incidence of total reflection while insonifying the semi-cylindrical boundary surfaces of the holes with ultrasonic sound beams, and adjusting the angle of incidence producing:
  two ultrasonic indications for an anti-rotation hole without a defect, one of the indications being caused by a first sub-beam reflected back upon itself at the periphery of the hole at an angle of incidence of 90°, and the other of the indications being caused by a second sub-beam totally reflected in vicinity of the corner; and a third ultrasonic indication for a defective anti-rotation hole, the third indication being caused by a third sub-beam totally reflected at the inner surfaces of the hub and at boundary surfaces of a defect.

14. Method according to claim 12, which comprises adjusting the incidence angle and the oblique angle of the US sound beam causing the angle of incidence at the defect location to be substantially 45°, relative to a perpendicular dropped onto the inner periphery of the hub in a region of incidence of the corner.

15. Apparatus for the ultrasonic testing of disc bodies shrunk onto shafts, the disc bodies having shrink-fitted seats adjoining the shafts, a shrinkage influence zone adjoining the seats, hubs adjoining the shafts and having inner surfaces subdivided into test regions and subregions, wheel discs adjoining the hubs, a rim of the wheel discs, and side walls of the wheel discs having contours being tapered radially outwardly from the hub to the wheel disc rim as seen in cross section, comprising a manipulator, at least one manipulator arm having a free end and being attached to the manipulator, a portion of said arm being movable in and out and being movable and adjustable in at least axial and transverse to axial directions, different probe mountings interchangeably fastened to said free end of said manipulator arm, said mountings comprising templates, said templates having shapes adapted to the contour of the side wall in vicinity of a respective subregion, ultrasonic angle beam probes disposed on said templates, and measuring feelers disposed on said templates.

16. Apparatus according to claim 15, wherein said direction transverse to the axial direction is the radial and height direction of the wheel discs.

17. Apparatus according to claim 15, wherein said manipulator arm is adjustable in circumferential direction of the wheel disc about the axis of the wheel disc and cover at least one part of the periphery of the wheel disc.

18. Apparatus according to claim 15, wherein at least two of said measuring feelers are disposed on a probe mounting, one of said feelers providing axial, and the other providing radial position control.

19. Apparatus according to claim 18, including at least one additional measuring feeler for obtaining a control signal.

20. Apparatus according to claim 15, wherein said feelers are inductive measuring feelers including a feeler head, an axially spring-loaded feeler pin having an end facing away from said feeler head, and a magnet core supported by said end of said pin for the distance-dependent detuning of an induction coil device.

21. Apparatus according to claim 18, wherein said feelers are inductive measuring feelers including a feeler head, an axially spring-loaded feeler pin having an end facing away from said feeler head, and a magnet core supported by said end of said pin for the distance-dependent detuning of an induction coil device.

22. Apparatus according to claim 19, wherein said feelers are inductive measuring feelers including a feeler head, an axially spring-loaded feeler pin having an end facing away from said feeler head, and a magnet core supported by said end of said pin for the distance-dependent detuning of an induction coil device.

23. Apparatus according to claim 15, wherein said angle beam probes are pneumatically resilient.

* * * * *